United States Patent [19]

Mauz et al.

[11] 4,007,282
[45] Feb. 8, 1977

[54] LOWERING LIPID AND SUGAR LEVELS IN THE BLOOD WITH A BIS(4-HYDROXYPHENYL)ALKANOIC ACID OR ESTER THEREOF

[75] Inventors: Otto Mauz, Liederbach, Taunus; Ernold Granzer, Kelkheim, Taunus, both of Germany

[73] Assignee: Hoechst Aktiengesellschaft, Frankfurt am Main, Germany

[22] Filed: June 7, 1973

[21] Appl. No.: 367,887

[30] Foreign Application Priority Data

June 10, 1972 Germany .................. 2228448

[52] U.S. Cl. .................. 424/308; 260/473 S; 260/520 R; 260/559 D; 424/317; 424/359; 424/360; 424/361; 424/363
[51] Int. Cl.[2] .................. A61K 31/19; A61K 31/215
[58] Field of Search .................. 260/520, 473 S; 424/317, 308

[56] References Cited

UNITED STATES PATENTS

| | | | |
|---|---|---|---|
| 2,933,520 | 4/1960 | Bader .................. | 260/473 S |
| 3,043,746 | 7/1962 | Cavallini et al. .................. | 424/317 X |
| 3,471,537 | 10/1969 | Berke et al. .................. | 424/317 X |
| 3,471,554 | 10/1969 | Holmen .................. | 260/520 |
| 3,499,008 | 3/1970 | Falet et al. .................. | 260/520 X |
| 3,514,472 | 5/1970 | Berke et al. .................. | 260/520 X |

FOREIGN PATENTS OR APPLICATIONS

| | | |
|---|---|---|
| 6,603,418 | 9/1966 | Netherlands |
| 1,047,039 | 11/1966 | United Kingdom |
| 1,134,337 | 11/1968 | United Kingdom |

*Primary Examiner*—Albert T. Meyers
*Assistant Examiner*—Vera C. Clarke
*Attorney, Agent, or Firm*—Curtis, Morris & Safford

[57] ABSTRACT

Pharmaceutical compositions acting on the metabolism which contain as active substance bis(4-hydroxyphenyl)alkanoic acids corresponding to the formulae I and II

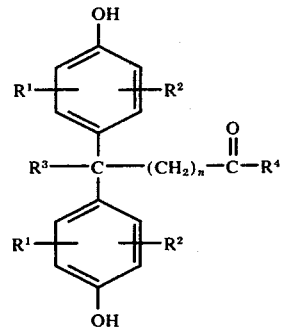

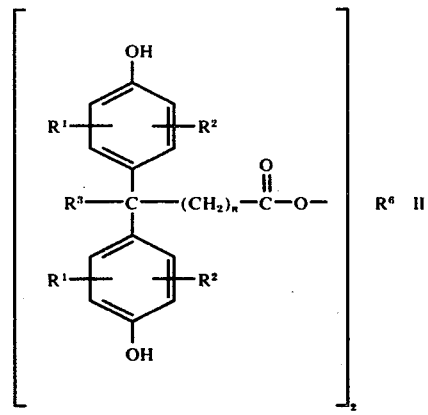

wherein $R^1$ and $R^2$ wich may be identical or different, each stands for a hydrogen or halogen atom or an alkyl group having 1 to 4 carbon atoms, $R^3$ stands for a hydrogen atom or an alkyl group having 1 to 3 carbon atoms, $R^4$ stands for hydroxy, alkoxy having 1 to 18 carbon atoms, phenyl-alkoxy having 1 to 4 alkyl carbon atoms, cycloalkoxy having 5 to 8 carbon atoms or a group of the formula

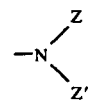

in which Z and Z', which may be identical or different, each stands for hydrogen, alkyl of 1 to 18 carbon atoms, phenyl or cycloalkyl of 5 to 8 carbon atoms, or both together with the nitrogen atom may form a heterocyclic ring, $R^6$ stands for an alkylene radical having 2 to 12 atoms and n stands for zero or an integer of 1 to 6, and process for preparing them.

13 Claims, No Drawings

LOWERING LIPID AND SUGAR LEVELS IN THE BLOOD WITH A BIS(4-HYDROXYPHENYL)ALKANOIC ACID OR ESTER THEREOF

The present invention relates to derivatives of bis(4-hydroxy-phenyl)alkanoic acid having an effect on the metabolism and corresponding to the formulae I and II

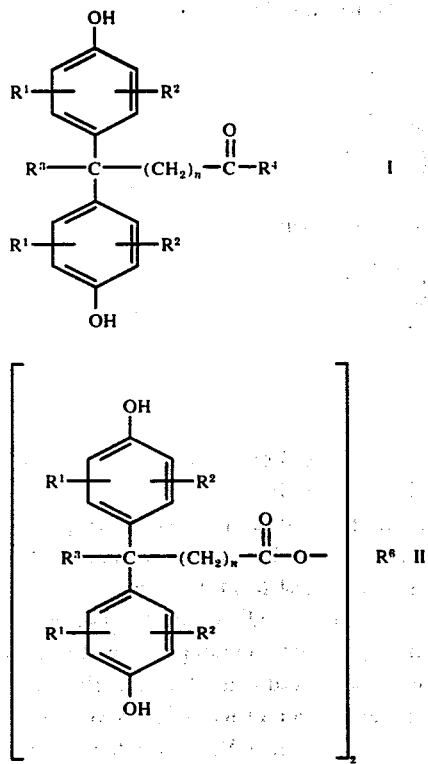

wherein
$R^1$ and $R^2$ which may be identical or different, each stands for a hydrogen or halogen atom, or an alkyl group having 1 to 4 carbon atoms,
$R^3$ stands for a hydrogen atom or an alkyl group having 1 to 3 carbon atoms,
$R^4$ stands for hydroxy, alkoxy having 1 to 18 carbon atoms, phenyl-alkoxy having 1 to 4 alkyl carbon atoms, cycloalkoxy having 5 to 8 carbon atoms or a group of the formula

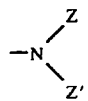

in which Z and Z′, which may be identical or different, each stands for hydrogen, alkyl of 1 to 18 carbon atoms, phenyl or cycloalkyl of 5 to 8 carbon atoms, or both together with the nitrogen atom may form a heterocyclic ring,
$R^6$ stands for an alkylene radical having 2 to 12 carbon atoms and
$n$ stands for zero or an integer of 1 to 6.

Some of the bis(4-hydroxy-phenyl)alkanoic acid derivatives coming within the formulae I and II have been disclosed in the art (for example M. H. Hubacher, J. Org. Chem. 24, 1949 (1959), A. J. Yu and A. R. Day, J. Org. Chem. 23, 1004 (1958), German Offenlegungsschrift Nos. 1,953,332 and 1,953,333, German Auslegeschrift No. 1,074,593, U.S. Pat. No. 2,933,520). Those compounds of formulae I and II which are known from the art have been disclosed to have utility as stabilizers for plastics or for the preparation of lacquer resins but also as fungicidal or bactericidal compositions. This utility suggests those known compounds to be mainly prepared from easily obtainable starting materials.

Compounds of formula I, in which $R^1$ is hydrogen, halogen or alkyl of 1 to 4 carbon atoms, $R^2$ is halogen or alkyl of 2 to 4 carbon atoms, $R^3$ is alkyl of 1 to 3 carbon atoms and $n$ is an integer of 2 to 6 and $R^4$ is defined as above, and compounds of formula II, in which $R^1$ is halogen or alkyl of 1 to 4 carbon atoms, $R^2$ is alkyl of 1 to 4 carbon atoms or halogen, or $R^1$ and $R^2$ each is hydrogen and $R^3$, $n$ and $R^6$ are defined as above, have not yet been disclosed.

Moreover, compounds of formula I, in which $R^1$ is hydrogen, $R^2$ is halogen or alkyl of 2 to 4 carbon atoms, $R^3$ is hydrogen or alkyl of 1 to 3 carbon atoms, $R^4$ is hydroxy, alkoxy of 4 carbon atoms or the group

wherein Z and Z′ are defined as above and $n$ is zero or 1, and compounds of formula II, in which $R^1$ is hydrogen, $R^2$ is halogen or alkyl of 1 to 4 carbon atoms, $n$ is an integer of 2 to 6 and $R^3$ and $R^6$ are defined as above, have not been disclosed as yet.

It has now been found that both the known and the novel bis(4-hydroxy-phenyl)alkanoic acid derivatives of formulae I and II have a therapeutic action on the metabolism and can therefore be used as medicaments, which utility was not taught by the state of the art.

Objects of the invention are therefore bis(4-hydroxyphenyl)alkanoic acid derivatives of formulae I and II, which have a therapeutic effect on the metabolism, their preparation as well as pharmaceutical compositions containing them as active substances.

In the formulae,
$R^1$ preferably stands for a hydrogen atom, a methyl or tert.-butyl group or a chlorine or bromine atom. Such a substituent may be in the ortho or meta position with respect to the hydroxy group, preferably in the ortho position.

$R^2$ is preferably in ortho position with respect to the hydroxy group; compounds in which $R^2$ stands for a methyl or tert.-butyl group or a hydrogen atom are preferred.

$R^3$ preferably stands for a hydrogen atom or a methyl group. Among the meanings given for $R^4$ in formula I, the hydroxy group and an alkoxy group having 1 to 12 carbon atoms are especially to be mentioned. Among the cyclo-alkoxy groups, those having 6 carbon atoms in the ring are preferred.

$R^6$ stands for a linear or branched alkylene radical, preferably an ethylene or polymethylene group, having 1 to 6 carbon atoms and $n$ stands in particular for zero, 1 or 2.

The compounds are prepared according to known methods.

The process for the manufacture of the compounds of formula I or II comprises a. reacting an ester of the formula III

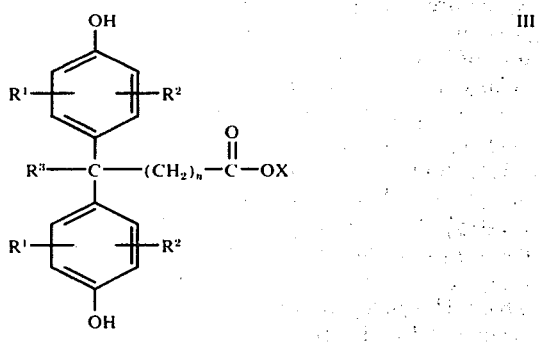

in which $R^1$, $R^2$, $R^3$ and $n$ are defined as above, and X stands for any organic radical, with a compound of the formula $H-R^4$, $R^4$ being defined as above, b. reacting a compound of the formula IV

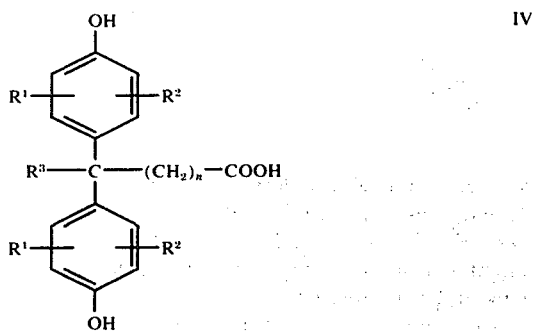

with a correspondingly substituted alcohol or amine, c. condensing a correspondingly substituted phenol with an aldehyde-carboxylic acid of the formula

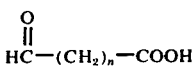

in which $n$ is defined as above, or an ester or amide thereof, and treating the reaction product of the formula V

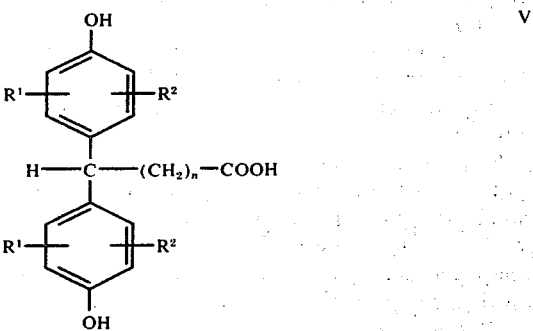

or the ester or amide thereof, where required, according to method (a) or (b), d. condensing a correspondingly substituted phenol with an α-keto-carboxylic acid of the formula

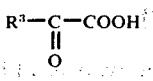

in which $R^3$ stands for alkyl of 1 to 3 carbon atoms, or an ester or amide thereof, and treating the reaction product of the formula VI

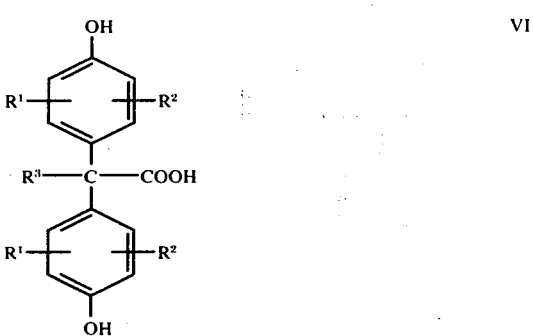

or the ester or amide thereof, where required, according to method (a) or (b), e. reacting a correspondingly substituted phenol with dichloroacetic acid and, where required, reacting the reaction product of the formula V, in which $n$ is zero, with a correspondingly substituted alcohol or amine, f. condensing a correspondingly substituted phenol with a ketomalonic acid ester and decarboxylating or hydrolyzing with an alkali metal hydroxide to yield a compound of the formula V, in which $n$ is zero, and where required treating the reaction product according to method (a) or (b), g. condensing a correspondingly substituted phenol with a ketocarboxylic acid of the formula $R^3 - CO - (CH_2)_n - COOH$ or an ester or amide thereof, in which $R^3$ stands for alkyl of 1 to 3 carbon atoms and $n$ for an integer of 1 to 6, and where required treating the reaction product of the formula VII

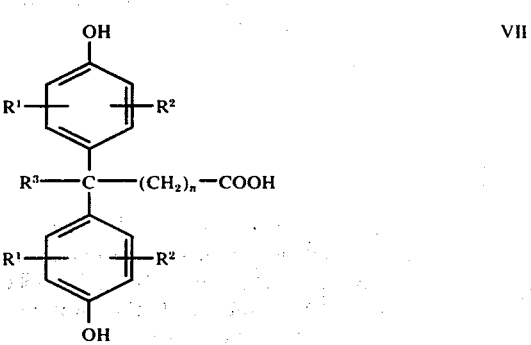

or an ester or amide thereof according to method (a) or (b), h. hydrolyzing a nitrile of the formula VIII

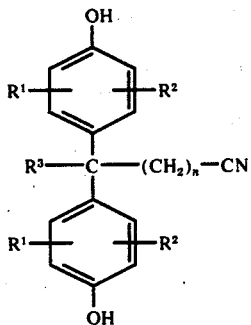   VIII and where required treating the reaction product according to method (a) or (b), i. reacting a correspondingly substituted bis-phenol-carboxylic acid of the formula IV or an ester thereof with a dihydric alcohol of the formula $R^6(OH)_2$, in which $R^6$ is defined as above, k. condensing a correspondingly substituted phenol with a bis (ketocarboxylic ester) of the formula

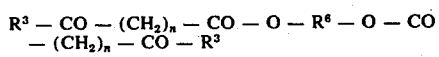

in which $R^3$ stands for an alkyl group of 1 to 3 carbon atoms, l. introducing an alkyl group having 1 to 4 carbon atoms or a halogen atom into a compound of the formula I or II, in which $R^1$ and/or $R^2$ stands for hydrogen.

The esters or acids of the formulae III and IV can be obtained according to methods (c), (d), (e), (f), (g) and (h). The transesterification, esterification, saponification or reaction with amines is carried out under the conditions known for that type of reactions.

The condensation reactions are carried out, with the exception of method (e), in an acid medium, preferably in the presence of hydrogen chloride, concentrated sulfuric acid or acid ion exchangers.

The starting compounds according to method (c) have been disclosed in the art. According to this method, there are preferably prepared compounds of formula V, in which $n$ is zero. The condensation reaction of glyoxylic acid with a phenol is carried out at a temperature below 50° C (cf. N. H. Hubacher, J. Org. Chem. 24, 1949 (1959)). Condensation with other aldehyde-carboxylic acids, for example with β-formyl-propionic acid or γ-keto-butyric acid, is also brought about at a moderately elevated temperature. When substituted phenols are reacted with aldehyde-carboxylic acids, the temperature chosen may advantageously range from 10° to 120° C, preferably from 20° to 65° C.

Of the α-keto-carboxylic acids to be mentioned according to method (d), pyruvic acid is preferred.

The condensation reaction with dichloracetic acid according to method (e) is advantageously carried out at a temperature of from 60° to 90° C in an alkaline medium.

According to method (f), 2,6-dialkylphenols are preferably condensed in the presence of concentrated sulfuric acid, a temperature of 0° C being preferred (cf. J. Org. Chem. 27, 3092 (1962)). Decarboxylation is preferably brought about using a potassium hydroxide solution.

The acetoacetic acid esters or amides thereof to be used, for example, as starting material according to method (g) are advantageously obtained by an addition reaction of corresponding monohydric alcohols or primary or secondary amines on diketene. These are condensed in a second step in the presence of hydrogen chloride with correspondingly substituted phenols at a temperature below 20° C (cf. DOS No. 1,953,332). In some cases, an addition of a water-binding substance is suitable. In order to accelerate the reaction, a catalyst, such as ethyl mercaptan, may be added.

The condensation reaction with other keto-carboxylic acids or the esters or amides thereof may advantageously be carried out according to A. J. Yu and A. R. Day, J. Org. Chem. 23, 1004 (1958) or DOS No. 1,953,332. The reaction products obtained may then be reacted further according to method (a) or (b).

The nitriles of formula VIII are, for example, obtained by condensing keto- or aldehyde-nitriles with correspondingly substituted phenols. Pyruvic acid nitrile, butanone-(2)-nitrile -(1) or butanone-(3)-nitrile-(1) are especially suitable. Condensation with aldehyde nitrile, for example β-cyanopropionaldehyde or the diacetal thereof or with γ-cyanobutyraldehyde, is preferably performed at a temperature of 20° to 100° C in an acid medium (hydrogen chloride, sulfuric acid, zinc chloride). The hydrolysis reaction of the nitriles is carried out under the conditions known for that type of reaction.

The bis-phenol-carboxylic acids or the esters thereof obtained according to methods (a) to (f) and (l) may be reacted with dihydric alcohols to yield the compounds of the formula II. Esterification is advantageously brought about in the presence of hydrogen chloride; transesterification is effected also with HCl or with other catalysts known for transesterification reactions.

The bis (acetoacetic acid esters) to be mentioned as possible starting compounds according to method (k) are obtained, for example, by an addition reaction of diketene on a corresponding dihydric alcohol (cf. DOS No. 1,953,333). In addition to bis-(acetoacetic acid esters), such as for example ethylene-glycol-1,2-bis-(acetoacetic acid ester) and hexane-diol-1,6-bis-(acetoacetic acid ester), there is also mentioned, for example, levulinic acid glycol ester. The condensation reaction is carried out in a manner analogous to DOS No. 1,953,333. As a catalyst, ethyl mercaptan is advantageously added.

The alkylation reaction according to method (l) is preferably carried out using alkyl halides. For the introduction of the tert.-butyl group, isobutylene is suitable in the presence of sulfuric acid or other Friedel-Crafts catalysts.

In addition to the compounds mentioned in the Examples, the following compounds are preferred according to the invention:

1. Bis(4-hydroxy-phenyl)ethanoic acid
2. Bis(4-hydroxy-3-methyl-phenyl)ethanoic acid
3. Bis(4-hydroxy-3,5-dimethyl-phenyl)ethanoic acid
4. Bis(4-hydroxy-3-methyl-5-tert.butyl-phenyl)ethanoic acid
5. Bis(4-hydroxy-3-methyl-phenyl)ethanoic acid ethyl ester
6. Bis(4-hydroxy-3,5-dibromo-phenyl)ethanoic acid
7. Bis(4-hydroxy-3,5-dibromo-phenyl)ethanoic acid n-butyl ester
8. Bis(4-hydroxy-3,5-dimethyl-phenyl)ethanoic acid n-butyl ester 9. Bis(4-hydroxy-3,5-di-tert.butyl-phenyl)ethanoic acid n-butyl ester
10. Bis(4-hydroxy-3,5-di-tert.butyl-phenyl)ethanoic acid isopropyl ester
11. Bis(4-hydroxy-3-tert.butyl-phenyl)ethanoic n-butyl amide
12. Bis(4-hydroxy-3,5-di-tert.butyl-phenyl)ethanoic acid n-octyl amide
13. 4,4-Bis(4'-hydroxy-3'-methyl-phenyl) butanoic acid
14. 2,2-Bis(4'-hydroxy-3'-tert.butyl-phenyl) propanoic acid
15. 2,2-Bis(4'-hydroxy-3'-tert.butyl-phenyl) propanoic acid n-butyl ester
16. 3,3-Bis(4'-hydroxy-phenyl) butanoic acid
17. 3,3-Bis (4'-hydroxy-3'-methyl-phenyl) butanoic acid methyl ester
18. 3,3-Bis(4'-hydroxy-3'-tert.butyl-6'-methyl-phenyl) butanoic acid methyl ester
19. 3,3-Bis(4'-hydroxy-3'-tert.butyl-phenyl) butanoic acid-cyclo-hexyl amide
20. 3,3-Bis(4'-hydroxy-3'-tert.butyl-phenyl) pentanoic acid
21. 4,4-Bis(4'-hydroxy-phenyl) pentanoic acid
22. 4,4-Bis(4'-hydroxy-3'-methyl-phenyl) pentanoic acid
23. 4,4-Bis(4'-hydroxy-3'-methyl-6'-tert.butyl-phenyl)-pentanoic acid
24. 4,4-Bis(4'-hydroxy-3'-methyl-phenyl) pentanoic acid methyl ester
25. 4,4-Bis(4'-hydroxy-3'-methyl-phenyl) pentanoic acid isopropyl ester
26. 4,4-Bis(4'-hydroxy-3'-tert.butyl-phenyl)pentanoic acid methyl ester
27. 4,4Bis(4'-hydroxy-3'-tert.butyl-phenyl) pentanoic acid tert.-butyl ester
28. 4,4-Bis(4'-hydroxy-3'-tert.butyl-phenyl) pentanoic acid n-butyl amide
29. 4,4-Bis(4'-hydroxy-3'-tert.butyl-phenyl) pentanoic acid diethyl amide
30. 4,4-Bis(4'-hydroxy-3'-tert.butyl-phenyl) pentanoic acid amide
31. 4,4-Bis(4'-hydroxy-3'-tert.butyl-phenyl) pentanoic acid cyclo-hexyl amide
32. Bis [2,2-bis(4'-hydroxy-3'methyl-phenyl) ethanoic acid] glycol ester
33. Bis [2,2-bis(4'-hydroxy-3'-tert.butyl-phenyl)ethanoic acid] butane-diol ester-(1,4)
34. Bis [2,2-bis(4'-hydroxy-3',5'-di-tert.butyl-phenyl) ethanoic acid] glycol ester
35. Bis [2,2-bis(4'-hydroxy-3',5'-di-tert.butyl-phenyl) ethanoic acid] hexane-diol ester-(1,6)
36. Bis [3,3-bis(4'-hydroxy-3'-tert.butyl-phenyl) butanoic acid] butane diol ester-(1,4)
37. Bis [3,3-bis(4'-hydroxy-3'-tert.butyl-phenyl) butanoic acid] dodecane diol ester-(1,12)
38. Bis [4,4-bis(4'-hydroxy-3',5'-di-tert.butyl-phenyl) pentanoic acid] glycol ester
39. Bis [4,4-bis)4'-hydroxy-3'-tert.butyl-phenyl) pentanoic acid] butane diol ester-(1,4)
40. Bis [4,4-bis(4'-hydroxy-3'-tert.butyl-5'-bromophenyl) pentanoic acid] glycol ester The compounds 1 to 13 are advantageously prepared according to methods (a), (b), (c), (e), (f), (h) and (l), whereas the preparation of the compounds 14 and 15 is especially suitable using, in addition to methods (a), (b) and (l), methods (d) and (h). According to methods (g) or (h) or (a) or (b) or (l), the bis(4'-hydroxy-phenyl)alkanoic acid derivatives 16 to 31 are obtained. The compounds 32 to 40 are prepared either according to method (i), (k) or (l).

The compounds of formulae I and II have therapeutic properties. They reduce serum lipid levels and may therefore be used for the therapy of primary hyperlipemia and certain secondary hyperlipemia which may, for example, occur in the case of diabetes, the most favorable effect on a disturbed diabetic metabolism being accompanied by a hypoglycemic activity of these compounds.

Since hyperlipemia is the most dangerous cause of coronary heart diseases and, generally speaking, elevated serum lipid values involve a great risk of causing arteriosclerotic diseases also of different localization and not only of the coronary vessels, the reduction of elevated serum lipid levels is extremely important for the prevention and therapy of arteriosclerosis, especially of the coronary heart vessels. Being able to reduce normal and elevated serum lipid levels in animals, the above specified substances are useful for the treatment and prevention of human and animal arteriosclerotic diseases, especially of the coronary vessels but also of other blood vessels.

While having an extremely low toxicity (see $LD_{50}$-values in Tables (2) and (3)), the compounds of formulae I and II are capable of reducing the lipid level in the blood considerably. Their hypolipemic activity could, inter alia, be demonstrated by the following animal tests:

1. Male rats having a normal serum lipid content were treated for eight days with different daily doses mentioned in Table 1. The values given in that Table stand for a change in the serum concentrations of certain lipid classes. The doses administered per os by means of an esophageal sound were 100, 30 and 10 mg/kg/day. Generally, prior to and after the treatment, blood samples were taken and the concentration of cholesterol in the serum was determined according to the method of Lauber and Richterich and that of triglycerides according to the method of Eggstein and Kreutz. In the examples of the following Table 1, the changes in the serum lipid values due to the treatment with the substances of the invention are defined as follows:
   a. The changes in percent in the final value of the treated group, referred to the initial value of the treated group, the initial value being 100 percent, and
   b. the change in the final value of the treated group, referred to the final value of an accompanying untreated control group, the untreated control group's value being defined as 100 percent. Thus, the value given in columns A is the change in percentage referred to the initial value, whereas the value given in columns B is the change in percentage of the treated group, referred to the untreated control group.

2. Dietetic-medicamentous hypercholesteremia of male rats

All the animals were fed with a diet food containing 2% of cholesterol, 2% of sodium cholate, 0.3% of methyl-thiouracil, 20% of coco fat and 44% of cane sugar. The serum lipid concentration of the animals treated with the compounds of the invention was compared to that of an untreated control group on the same diet, which diet causes the serum cholesteral concentration to rise within 1 week to about 10 times the initial value, that of the serum triglycerides to 3 times and that of the phospho-lipids in the serum to 4 times the initial value. The lipid phosphorus was determined according to the method of Messrs. Boehringer Mannheim W. Germany. At the same time as the diet was offered, the compounds of the invention were administered once a day to groups of rats, each containing 10 animals, over a period of 8 days by means of an esophageal sound. The change in percentage in the serum lipid concentration as compared to the control group (diet without active substance) is indicated in Table 2.

3. The hypertriglyceridemia induced by carbohydrates and initiated by fructose doses in male rats was substantially reduced by a 3-day oral pre-treatment with the substances of the invention in comparison to untreated control animals (Table 3).

TABLE 3-continued

Action on the hypertriglyceridemia induced by carbohydrates

Change in percentage of hypertriglyceridemia induced by carbohydrates in male rats by administering

| Compound of example | 100 mg/kg | 30 mg/kg | 10 mg/kg | in mg/kg $LD_{50}$ mice p.o. |
|---|---|---|---|---|
| 17 | −10 | | | >8000 |

The favorable action of the compounds of formulae I and II on the disturbed diabetic metabolism is not only based on a normalization of the disturbed lipid metabolism, i.e. on their hypolipidemic activity, but also on an action on the carbohydrate metabolism.

The hypoglycemic activity of some bis(4-hydroxyphenyl) alkanoic acid derivatives of formulae I and II could be established by administering once a day, over 3 days, 100 mg of the active compound per kg of test animal to rats that had been fed fructose doses and by taking blood samples 24 hours after the last administration in order to determine the blood sugar level by means of an autoanalyzer.

The lowering of the blood sugar content indicated in following Table 4 refers to a control group treated with placebos (blank doses).

TABLE 1

Reduction of serum lipid values in normolipemic rats

Change in percentage after oral administration of 8 doses to male rats in mg/kg/day

| | 100 | | | | 30 | | | | 10 | | | |
|---|---|---|---|---|---|---|---|---|---|---|---|---|
| Compound of Example | serum cholesterol | | serum triglyceride | | serum cholesterol | | serum triglyceride | | serum cholesterol | | serum triglyceride | |
| | A | B | A | B | A | B | A | B | A | B | A | B |
| Clofibrat | −22 | −15 | −48 | −37 | | | | | | | | |
| 3 | −61 | −52 | −70 | −60 | −32 | −22 | −39 | −46 | −24 | −21 | | −29 |
| 8 | −43 | −26 | −23 | | −14 | −16 | | −22 | − 8 | −13 | | −25 |
| 7 | −29 | −26 | −53 | −23 | | | | | | | | |
| 15 | −37 | −20 | −36 | −13 | −13 | −10 | −32 | −37 | − 8 | − 3 | −20 | −34 |
| 16 | −20 | −21 | −27 | −26 | −10 | −15 | | −32 | | | | |
| 18 | −48 | −33 | −51 | −17 | | | | | | | | |

TABLE 2

Action on the dietetic-medicamentous hyperlipemia of male rats

| Compound of Example | dose mg/kg/day p.o. | serum cholesterol | serum triglyceride | serum lipid phosphorus | p.o. $LD_{50}$ mice (mg/kg) |
|---|---|---|---|---|---|
| Colfibrat | 100 | 0 | −27 | −12 | 2000−25000 |
| 3 | 100 | −23 | −44 | −26 | 6000−8000 |
| 8 | 100 | −36 | −39 | −37 | >8000 |
| 4 | 100 | −29 | −21 | −25 | |
| 1 | 100 | −11 | −18 | −15 | |
| 2 | 100 | −19 | −13 | −9 | 2000 |
| 7 | 100 | −30 | −34 | −30 | >8000 |
| 15 | 100 | −57 | −34 | −53 | >8000 |
| 19 | 100 | −17 | −28 | −17 | 4000 |
| 14 | 100 | −36 | −13 | −25 | 4000 |
| 18 | 100 | −36 | −19 | −37 | 4340 |

TABLE 3

Action on the hypertriglyceridemia induced by carbohydrates

Change in percentage of hypertriglyceridemia induced by carbohydrates in male rats by administering

| Compound of example | 100 mg/kg | 30 mg/kg | 10 mg/kg | in mg/kg $LD_{50}$ mice p.o. |
|---|---|---|---|---|
| Colfibrat | −15 | | | 2000−2500 |
| 3 | −37 | −36 | | 6000−8000 |
| 2 | | −63 | | 2000 |
| 8 | | | | >8000 |
| 13 | | −17 | | 8000 |
| 7 | −35 | −19 | | >8000 |
| 15 | −28 | | | >8000 |
| 19 | −27 | | | 4000 |
| 16 | | −24 | | 4338 |
| 18 | −46 | −34 | | 4340 |
| 21 | | | | 4088 |

TABLE 4

| Compound of Example | lowering of the blood sugar level in per cent |
|---|---|
| 3 | −15 |
| 5 | −30 |
| 7 | −24 |
| 17 | −18 |

TABLE 4-continued

| Compound of Example | lowering of the blood sugar level in per cent |
| --- | --- |
| 19 | −20 |

Owing to their favorable effects on the lipid and carbohydrate metabolism, the compounds of formulae I and II are especially suitable as antidiabetics and hypolipemics.

The bis(4-hydroxy-phenyl)alkanoic acid derivatives of formulae I and II may be administered as active substances either as such or in admixture with pharmacologically acceptable carriers, an oral dosage unit form being preferred. For this purpose, the active substances are mixed with known excipients and brought into suitable dosage unit forms according to known methods, for example into granules, tablets, hard gelatine capsules, emulsions, aqueous or oily suspensions or aqueous or oily solutions. As inert carriers and fillers, there may for example be mentioned diluents, such as magnesium carbonate, talcum or lactose; granulating and disintegrating agents, such as starch or alginic acid; binders, for example starch or gelatin, and lubricants, such as stearic acid, talcum or magnesium stearate, for the preparation of dry compositions. The compositions may be obtained by dry or moist granulation and may be coated to retard disintegration or absorption in the gastro-intestinal tract, thus assuring a prolonged action. Suspensions, syrups or elixirs may also contain the active substance in admixture with usual excipients, for example methyl cellulose, tragacanth or sodium alginate. As wetting agents, there may for example be mentioned lecithin or polyoxy-ethylene stearate. Oily carriers or solvents are especially vegetable or animal oils, for example peanut or sunflower oil or codliver oil. Moreover, the compositions may contain the usual additives, such as sweetening agents, flavoring agents, dyestuffs or preserving agents.

The daily dosage unit ranges from 0.1 to 4 g, preferably from 0.5 to 2 g, which is preferably administered in several portions each ranging from 0.1 to 1 g, preferably from 250 mg to 500 mg, two to four times per day.

A special utility of the novel compounds is that they can be combined with other active substances, for examples with the following ones:

Antidiabetics, such as glycodiazine, tolbutamide, glibenclamide or agents acting on the circulatory system, especially those dilating the coronary vessels, such as chromonar or prenylamine; blood sugar lowering substances, such as Reserpin, α-methyl-dopa or clonidines; further agents lowering the lipid level; geriatrics; or psychopharmaceuticals, for example chlorodiazepoxide, diazepam, meprobamate or vitamins.

The following Examples serve to illustrate the invention.

EXAMPLE 1

3,3-Bis(4'-hydroxy-3'-methyl-phenyl)butanoic acid

A suspension of 314 g of 3,3-bis(4'-hydroxy-3'-methyl-phenyl) butanoic acid methyl ester (m.p. 162° C) and 80 g of sodium hydroxide in 1 liter of water was refluxed for 8 hours while stirring. After cooling to 40°–50° C the suspension was acidified with hydrochloric acid and the 3,3-bis(4'-hydroxy-3'-methylphenyl) butanoic acid was extracted with ether. The ether phase was washed several times with water and then the ether was removed in vacuo. The remaining residue was the white crystallized 3,3-bis(4'-hydroxy-3'-methylphenyl)butanoic acid, m.p. 130° C.

Analysis: $C_{18}H_{20}O_4$: Found: C, 71.1%; H, 6.5%; acid number 189. Calculated: 72.0%; H, 6.7%; acid number 186.

EXAMPLE 2

3,3-Bis(4'-hydroxy-3'-tert.-butyl-phenyl)butanoic acid 200 g of 3,3-bis(4'-hydroxy-3'-tert.-butylphenyl)-butanoic acid methyl ester (m.p. 82° C) were added to a solution of 40 g of sodium hydroxide in 600 ml of ethanol and the mixture was refluxed. After cooling to room temperature, the mixture was acidified with hydrochloric acid. The alcohol was removed by distillation and the solid residue was dissolved in hot toluene. The hot solution was filtered. Upon cooling, the 3,3-bis(4'-hydroxy-3'-tert.butyl-phenyl)butanoic acid precipitated from the toluene solution, m.p. 156° C.

Analysis: $C_{24}H_{32}O_4$: Found: C, 75.5%; H, 8.7%. Calculated: C, 75.0%; H, 8.3%.

EXAMPLE 3 a. Bis(4'-hydroxy-3',5'-di-tert.butyl-phenyl)ethanoic acid

A solution of 129 g of dichloracetic acid in 40 g of methanol was added dropwise in portions at 85° C within 6 hours to a suspension of 103 g of 2,6-di-tert.-butyl-phenol in 200 g of methanol and 147 g of sodium hydroxide. The mixture was then stirred for about 20 hours at 80° C. After cooling to 20° C, it was acidified with dilute hydrochloric acid (pH 5–6), whereupon the crude bis(4'-hydroxy-3',5'-di-tert.-butylphenyl) ethanoic acid of a yellow orange color precipitated. After drying and subsequent recrystallization from cyclohexane, the pure acid was obtained as a white crystallized compound, m.p. 211° C.

Analysis: $C_{30}H_{44}O_4$: Found: C, 76.9%; O, 13.5%; H, 9.3%. Calculated: C, 77.0%; O, 13.7%; H, 9.4%.

b. A four-necked flask provided with stirrer, thermometer, reflux condenser and dropping funnel was filled with a solution of 206 g of 2.6-di-tert.-butyl-phenol (1 mol) and 50 g of 78% glyoxylic acid (0.5) in 1 liter of glacial acetic acid, and 74 g of concentrated sulfuric acid were added dropwise in such a manner that the temperature did not exceed 40° C. After sulfuric acid had been added, stirring was continued for about 2 hours at 40° C. The resulting precipitate was suction-filtered and washed to neutral with water. The crude product was dried at 80° C in vacuo.

100 g of bis(4-hydroxy-3,5-di-tert.-butylphenyl)ethanoic acid were refluxed for 2 hours in 200 ml of absolute alcohol. The precipitate which had separated after cooling was suction-filtered, washed with absolute ethanol and dried at 100° C in vacuo. The substance melted at 210° C.

The crude product could also be purified by recrystallization from cyclohexane. After having been dried at 100° C in vacuo, the bis(4-hydroxy-3,5-di-tert.-butylphenyl)ethanoic acid was obtained, m.p. 212° C.

Analysis: $C_{30}H_{44}O_4$: Found: C, 77.1%; H, 9.3%. Calculated: C, 77.0%; H, 9.4%.

When the bis(4-hydroxy-3,5-di-tert.-butylphenyl)ethanoic acid was dried at room temperature, it formed with cyclohexane a crystallized addition product.

EXAMPLE 4

Bis(4'-hydroxy-3'-tert.-butyl-phenyl)ethanoic acid

A solution of 82 g of glyoxylic acid . ½ H$_2$O (1 mol) and 375 g of o-tert.-butyl-phenol (2.5 mols) in 300 ml of benzene was saturated at 40° C wtih gaseous hydrogen chloride and condensed at this temperature. From time to time, saturation was completed by adding a small amount of gaseous hydrogen chloride. After about 40 hours, condensation was complete. The precipitate which had separated upon cooling was suction-filtered and recrystallized from methylene chloride. The yield was 190 g (52%, calculated on glyoxylic acid), m.p. 173° C.

Analysis: C$_{22}$H$_{28}$O$_4$: Found: C, 74.0%; H, 7.6%. Calculated: C, 74.1%; H, 7.8%.

EXAMPLE 5

Bis(4'-hydroxy-3'-tert.-butyl-phenyl)ethanoic acid n-butyl ester 35.6 g of bis(4-hydroxy-3-tert.-butyl-phenyl)ethanoic acid (0.1 mol) were dissolved in a mixture of 222 g of n-butanol and 240 g of toluene. As an esterification catalyst, 1 g of p-toluene-sulfonic acid was added. Azeotropic distillation was continued until 1.8 mol of water had separated at the separator. The butanol-toluene phase was washed with 10% sodium bicarbonate solution and then with water. The solvent mixture was distilled off and the residue was dissolved and precipitated in 300 ml of heptane. After distillation of the solvent, 38 g (92%, calculated on the acid used) of bis(4'-hydroxy-3'-tert-butyl-phenyl)ethanoic acid n-butyl ester were obtained, m.p. 124° C.

Analysis: C$_{26}$H$_{36}$O$_4$: Found: C, 75.3%; H, 9.0%. Calculated: C, 75.6%; H, 8.8%.

EXAMPLE 6

3,3-bis(4'-hydroxy-3'-tert.-butyl-phenyl)butanoic acid isopropyl ester

A four-necked flask provided with stirrer, reflux condenser, thermometer and gas inlet pipe was filled with 300 g of o-tert.-butyl-phenol (2 mols), 144 g of acetoacetic acid isopropyl ester (1 mol) and 0.72 g of ethyl-mercaptan. The reaction mixture was cooled to 10° C and saturated while stirring with hydrogen chloride at this temperature. The condensation was weakly exothermal. After about 10 hours of condensation, 1 liter of toluene was added and condensation water formed was distilled off in an azeotropic mixture. After cooling of the toluene solution, the final product precipitated as a crystallized white substance.

Yield : 358 g (84%, calculated on the ester used), m.p. 176° C

Found: C, 75.9%; H, 8.9%. Calculated: C, 76.0%; H, 8.9%.

EXAMPLE 7

3,3-bis(4'-hydroxy-3'-tert.-butyl-phenyl)butanoic acid butyl ester

At 10° C, gaseous hydrogen chloride was introduced into a mixture of 300 g of o-tert.-butyl-phenol (2 mols), 158 g of acetoacetic acid n-butyl ester and 0.5 g of ethyl mercaptan. The solution was condensed while stirring at 10° C for about 48 hours. Subsequently, condensation water and unreacted o-tert.-butyl-phenol were distilled off in vacuo. The resinous residue was dissolved and precipitated in cyclohexane.

Yield: 372 g (84%), m.p. 103° C.

Analysis: C$_{28}$H$_{40}$O$_4$: Found: C, 77.3%; H, 9.6%. Calculated: C, 77.6%; H, 9.1%.

EXAMPLE 8

3,3-bis(4'-hydroxy-3'-methyl-phenyl)butanoic acid n-butyl ester 2160 g of o-cresol (20 mols), 760 g of acetoacetic acid n-butyl ester (5 mols) and 0.76 g of ethyl-mercaptan were cooled to 10° C and saturated with gaseous hydrogen chloride. After a condensation time of about 20 hours at 10° C, hydrochloric acid and o-cresol were distilled off by means of a water jet pump. The temperature was then slowly increased from 20° to 150° C. The resin-like product obtained after distillation was recrystallized in 3 liters of xylene while adding a small amount of kieselguhr.

Yield: 1220 g (68%, calculated on the acetoacetic acid n-butyl ester used), m.p. 116° C Analysis: C$_{22}$H$_{28}$O$_4$: Found: C, 73.9%; H, 7.9%. Calculated: C, 74.1%, H, 7.9%.

EXAMPLE 9

3,3-Bis(4'-hydroxy-3'-tert.-butyl-phenyl)butanoic acid cyclohexyl ester

In a four-necked flask, 300 g of o-tert.-butyl-phenol (2 mols), 184 of acetoacetic acid cyclohexyl ester (1 mol) and 0.9 g of ethyl-mercaptan were mixed and the mixture was saturated at 10° C with gaseous hydrogen chloride. After a condensation time of 24 hours at 5°–10° C, toluene was added and condensation water was distilled off in an azeotropic mixture. Upon cooling, the 3,3-bis(4'-hydroxy-3'-tert.-butyl-phenyl) butanoic acid cyclohexyl ester precipitated from the toluene in crystals.

Yield: 384 g (82%, calculated on the acetoacetic acid ester used), m.p. 168° C

Analysis: C$_{30}$H$_{42}$O$_4$: Found: C, 77.9%; H, 9.1%. Calculated: C, 77.3%; H, 9.0%.

EXAMPLE 10

3,3-Bis(4'-hydroxy-3',5'-dimethyl-phenyl)butanoic acid dodecyl ester

In a four-necked flask, 122 g of 2,6-dimethyl-phenol (1 mol), 135 g of acetoacetic acid dodecyl ester (0.5 mol) and 0.7 g of ethyl mercaptan were mixed and at 10° C gaseous hydrogen chloride was passed through this mixture for 8 hours. The mixture was stirred for 24 hours at 10° C, then toluene was added and the resulting water was distilled off in an azeotropic mixture. Upon cooling, the 3,3-bis(4'-hydroxy-3',5'-dimethyl-phenyl)butanoic acid dodecyl ester precipitated from the toluene solution in crystals.

Yield: 176 g (71%, calculated on the acetoacetic acid ester used), m.p. 121° C.

Analysis: C$_{32}$H$_{48}$O$_4$: Found: C, 77.4%; H, 9.8%. Calculated: C, 77.4%; H, 9.6%.

EXAMPLE 11

Bis [3,3-bis(4'-hydroxy-3-tert.-butyl-phenyl)butanoic acid]2,2-dimethyl-propane-diol-1,3 ester As disclosed in Example 16, 450 g of o-tert.butyl-phenol (3 mols), 136 g of 2,2-dimethyl-propane-diol-1,3-bis(acetoacetic acid ester)(½ mol) and 0.68 g of ethyl mercaptan were saturated at 10° C with hydrogen chloride and condensed for 28 hours at 10° C. The reaction product was worked up as in Example 16. The crude product was recrystallized from toluene.

Yield: 302 g (62%, calculated on acetoacetic acid ester) m.p. 96° C

Analysis: $C_{53}H_{72}O_8$: Calculated: C, 76.2%; H, 8.6%. Found: C, 77.0%; H, 8.9%.

EXAMPLE 12

3,3-Bis(4'-hydroxy-3'-tert.-butyl-phenyl)butanoic acid benzyl ester

In a reaction flask, 450 g of o-tert.-butyl-phenol (3 mols), 192 g of acetoacetic acid benzyl ester (1 mol) and 0.98 g of ethyl mercaptan were mixed and condensed at 10° C for 48 hours in the presence of gaseous hydrogen chloride. Subsequently, the hydrochloric acid was eliminated at about 15° C by means of a water jet pump under a pressure of 10 mm mercury; the bath temperature was then slowly raised to 190° C and at a pressure of 5 mm mercury the remaining o-tert.-butyl-phenol was distilled off. The resulting residue was a brittle resin of brown color. This crude product was dissolved in toluene, brightened by means of bleaching earth and, after the bleaching earth had been filtered off, the compound was precipitated with hexane.

Yield: 394 g (84%, calculated on acetoacetic acid ester used), m.p. 113° C

Analysis: $C_{31}H_{38}O_4$: Found: C, 78.1%; H, 7.9%. Calculated: C, 78.5%; H, 8.0%.

EXAMPLE 13

3,3-Bis(4'-hydroxy-3'-tert.-butyl-phenyl)butanoic acid n-butylamide 158 g of acetoacetic acid butyl amide (1 mol), 600 g of 0-tert.-butyl-phenol (4 mols) and 1 g of ethyl mercaptan were mixed and saturated at 10° C with anhydrous gaseous hydrogen chloride. After a condensation time of about 40 hours, water which had formed and then excess o-tert.-butyl-phenol were eliminated in vacuo. The residue was recrystallized from xylene.

Yield: 263 g (60%, calculated on acetoacetic acid butyl amide used), m.p. 215° C Analysis: $C_{28}H_{41}NO_3$: Found: C, 76.6%; H, 9.4%. Calculated: C, 76.6%; H, 9.3%.

EXAMPLE 14

4,4-Bis(4'-hydroxy-3'-tert.-butyl-phenyl)pentanoic acid 600 g o-tert.-butyl-phenol, levulinic acid and 0.6 g of ethyl mercaptan were saturated at 20° C with gaseous hydrogen chloride and condensed for about 48 hours at room temperature. After condensation was complete, water and excess o-tert.-butyl-phenol were first distilled off by means of a water jet pump (10 mm mercury) and then by means of an oil pump (1 mm mercury). The temperature of the heating bath was gradually raised to 150° C. After cooling of the residue, a brittle resin of yellow color was obtained. After dissolution and precipitation from 500 ml of toluene, 300 g (80%) of a white crystallized compound were obtained, m.p. 155° C.

Analysis: $C_{25}H_{34}O_4$: Found: C, 75.3%; H, 8.8%. Calculated: C, 75.4%; H, 8.5%.

EXAMPLE 15

4,4-Bis(4'-hydroxy-3'-tert.-butyl-phenyl)pentanoic acid n-butyl ester 39.8 g of 4,4-bis(4'-hydroxy-3'-tert.-butyl-phenyl)pentanoic acid were dissolved in 222 g of n-bitanol and 228 g of toluene and 1 g of p-toluene-sulfonic acid was added as an esterification catalyst. Azeotropic distillation was continued until no more water distilled over. After toluene and butanol had been distilled off, a resin-like residue was obtained. After recrystallization from hexane, the 4,4-bis(4'-hydroxy-3'-tert.-butyl-phenyl)pentanoic acid n-butyl ester was obtained as a white crystallized substance.

Yield: 27.9 g (61.5%), m.p. 123° C

Found: C, 76.7%; H, 9.2%. Calculated: C, 76.6%; H, 9.3%.

EXAMPLE 16

Bis [3,3-bis(4'-hydroxy-3'-tert.-butyl-phenyl)butanoic acid] glycol ester

A reaction flask was filled with 1200 g of o-tert.-butyl-phenol (8 mols) and 230 g of ethylene-glycol-1,2-bis(acetoacetic acid ester), $n_D^{20} = 1.4535$ (1 mol). The reaction mixture was cooled to 10° C, 1,14 g of ethyl mercaptan were added and then anhydrous hydrogen chloride was fed in until saturation was reached. By cooling with ice water, the condensation temperature was maintained at 10° C for 24 hours. The aqueous hydrochloric acid was eliminated at 15°–20° C by means of a water jet pump. The temperature was then slowly raised to 180° C and excess o-tert.-butyl-phenol was distilled off. After cooling of the resin-like crude-product, recrystallization was performed from toluene.

Yield: 595 g (75%, calculated on acetoacetic acid ester), m.p. 170° C

Analysis: $C_{50}H_{66}O_8$: Found: C, 75.9%, H, 8.3%. Calculated: C, 75.5%; H, 8.3%.

EXAMPLE 17

Bis [3,3-bis(4'-hydroxy-3'-tert.-butyl-phenyl)butanoic acid]hexane-diol-1,6 ester According to Example 16, a mixture of 450 g of o-tert.-butyl-phenol (3 mols), 143 g of hexane-diol-1,6-bis(acetoacetic acid ester) (0.5 mol) and 0.6 g of ethyl mercaptan was condensed at 10° C for 18 hours with hydrogen chloride. After water and excess o-tert.-butyl-phenol had been distilled off, 390 g of a brown brittle resin were obtained. After recrystallization from acetone, 272 g (64%, calculated on acetoacetic acid ester) of a crystallized product were obtained, m.p. 104° C.

Analysis: $C_{54}H_{74}O_8$: Found: C, 75.2%; H, 8.1%. Calculated: C, 76.0%; H, 8.7%.

EXAMPLE 18

Bis [4,4-bis(4'hydroxy-3'-tert.-butyl-phenyl)pentanoic acid] glycol ester

A mixture of 64.5 g of levulinic acid glycol ester, 300 g of o-tert.-butyl-phenol and 0.3 g of ethyl mercaptan were saturated at 10° C for 16 hours with gaseous hydrogen chloride. Condensation was continued for about 48 hours at 10° C. The resulting condensation water and excess o-tert.-butyl-phenol were distilled off. The resin-like residue was recrystallized from heptane to afford the bis [4,4-bis(4'-hydroxy-3'-tert.-butyl-phenyl)pentanoic acid] glycol ester, m.p. 132° C.

Yield: 140 g.

Analysis: $C_{52}H_{70}O_8$: Found: C, 76.0% H, 8.4%. Calculated: C, 75.8%; H, 8.5%.

EXAMPLE 19

4,4-Bis(4'-hydroxy-phenyl)pentanoic acid 376 g of phenol (4 mols), 116 g of levulinic acid (1 mol) and 0.4 ml of ethyl mercaptan were condensed, while stirring and simultaneously feeding in hydrogen chloride, for about 48 hours at 30°–40° C. The viscous reaction solution was taken up in ether and the ether phase was washed first with a sodium bicarbonate solution and then with water. After the ether had been eliminated, a brittle resin-like solid was obtained, m.p. 171°–173° C.

Analysis: $C_{17}H_{18}O_4$: Found: C, 70.8%; H, 6.0%. Calculated: C, 71.3%; H, 6.3%.

EXAMPLE 20

Bis(4'-hydroxy-3',5'-di-tert.-butyl-phenyl)ethanoic acid 103 g of 2,6-di-tert.-butyl-phenol (0.5 mol) and 21 g of glyoxylic acid (0.25 mol) of (CHO.COOH) . ½ $H_2O$) were dissolved in 300 ml of carbon tetrachloride and stirred at 50° C for about 40 hours. During the first 6 hours, a weak hydrogen chloride stream was passed through the solution, later saturation was completed from time to time by feeding in hydrogen chloride. After condensation was complete, the solvent was eliminated. The product obtained in a pasty form was dissolved and precipitated several times from hexane. The crystallized compound having a faint yellowish tinge melted at 211° C.

Analysis: $C_{30}H_{44}O_4$: Found: C, 76.4%, H, 9.1%. Calculated: C, 76.9%; H, 9.4%.

EXAMPLE 21

Bis [3,3-bis(4'-hydroxy-3'-tert.-butyl-5'-bromophenyl) butanoic acid] glycol ester 79.4 g of bis [3,3-bis(4'-hydroxy-3'-tert.-butyl-phenyl) butanoic acid] glycol ester (0.1 mol) were dissolved in 400 ml of carbon disulfide. 32 g of bromine in 20 ml of carbon disulfide were slowly added dropwise to this solution at −5° to 0° C. Stirring was then continued for about 6 hours at 20° – 25° C. After the solvent had been distilled off, a solid residue having a faint pink tinge was obtained, m.p. 69°–73° C.

Analysis: $C_{50}H_{62}Br_4O_8$: Found: C, 53.1%, H, 5.2%, Br, 27.3%. Calculated: C, 54.0%; H, 5.6%; Br, 38.8%.

EXAMPLE 22

5,5-Bis(4'-hydroxy-3',5'-dimethyl-phenyl)hexanoic acid methyl ester 244 g of 2,6-dimethyl-phenol (2 mols), 72 g of acetyl-butyric acid methyl ester (0.5 mol) and 0.5 g of ethyl mercaptan were mixed and while stirring anhydrous hydrogen chloride was fed in at 10° C for 6 hours. After 48 hours, the solid crystallized product was extracted with cold hexane, whereupon the 2,6-dimethyl-phenol entered into solution. The resulting undissolved residue was filtered off and recrystallized from a hydrocarbon fraction boiling between 140 and 150° C (Varsol) with an addition of charcoal.

Yield: 150 g, m.p. 153° C

Analysis: $C_{23}H_{30}O_4$: Found: C, 75%; H, 8.3%. Calculated: C, 74.5%; H, 8.1%.

EXAMPLE 23

A compound as obtained according to Examples 1 to 22 was compressed into tablets such that each tablet contained 250 mg and could be administered orally as individual dosage unit.

EXAMPLE 24

A compound as obtained according to Examples 1 to 22 was used to fill hard gelatin capsules of a suitable size at a fill weight of 250 mg per capsule.

EXAMPLE 25

A compound as obtained according to Examples 1 to 22 was mixed with lactose and the mixture was used to fill hard gelatin capsules of a suitable size at a mixing ratio of 250 mg of active substance to 100 mg of lactose per capsule.

EXAMPLE 26

A compound as obtained according to Examples 1 to 22 was compressed into tablets such that each tablet contained 500 mg of active substance.

EXAMPLE 27

A ground compound as obtained according to Examples 1 to 22 was mixed with lactose powder and ascorbic acid and the resulting mixture was used to fill hard gelatin capsules such that each capsule contained 500 mg of active substance, 200 mg of lactose and 20 mg of ascorbic acid.

EXAMPLE 28

100 g of a compound as obtained according to Examples 1 to 22, 20 g of calcium sulfate and 50 g of cane sugar were intimately mixed with each other and granulated with a hot 10% gelatin solution. The moist granules were screened through a 16 mesh U.S. standard sieve directly onto drying troughs. The granules were dried at 49° C and screened through a 20 mesh sieve. The dried granules were then blended with 30 g of starch, 10 g of talcum and 6 g of stearin and the mixture was screened through a 60 mesh U.S. standard sieve. Subsequently, it was compressed into tablets such that each tablet contained 200 mg of active substance.

EXAMPLE 29

200 mg of a compound as obtained according to Examples 1 to 22 were stirred with 600 mg of peanut oil to form a stiff paste which was used to fill soft gelatin capsules.

EXAMPLE 30

500 g of a compound as obtained according to Examples 1 to 22 were made into a paste with 500 g of sunflower oil to form a stiff mass which was used to fill soft gelatin capsules such that each capsule contained 200 mg of active compound.

EXAMPLE 31

To make an orally administerable composition, 250 g of placebo granules consisting of 60% of lactose and 40% of starch were blended with a compound as obtained according to Examples 1 to 22 and then 30 g of talcum and 20 g of magnesium stearate were added.

The resulting mixture was compressed into tablets in a rotary tableting machine.

EXAMPLE 32

The following ingredients were blended with each other and compressed into tablets: A ground compound as obtained according to Examples 1 to 22 (250 mg), corn starch (140 mg), lactose powder (45 mg), talcum (30 mg), amylopectin (30 mg) and magnesium stearate (5 mg).

EXAMPLE 33

Linguettes were obtained by combining the following ingredients: An active compound as obtained according to Examples 1 to 22 (300 mg), magnesium stearate (15 mg), lactose (125 mg). These ingredients were thoroughly blended and used to fill hard gelatin capsules.

EXAMPLE 34

A mixture of 550 g of a compound as obtained according to Examples 1 to 22, 95 g of corn starch, 44 g of alginic acid and 3.6 g of magnesium stearate was molded into shaped structures which were then broken up into granules. The granules were screened through a 8 mesh U.S. standard sieve and blended with 3.4 g magnesium stearate. The resulting mixture was then compressed into tablets.

EXAMPLE 35

A mixture of 150 g of a compound as obtained according to Examples 1 to 22 and 44 g of corn oil was blended with 3.1 g of gum Arabic and 1.6 g of tragacanth. To this mixture, a solution of 0.1 g of a condensation product of cetyl alcohol and polyoxy-ethylene, 40 g of cane sugar, 0.025 g of propyl parahydroxy benzoate, 0.35 g of methyl parahydroxy benzoate and 108 g of water was slowly added. After a suitable flavoring agent and, where required, a suitable dyestuff had been added, the mixture was homogenized on a conventional device to form an emulsion suitable for oral administration. This emulsion was used to fill suitable containers.

EXAMPLE 36

110 g of a compound as obtained according to Examples 1 to 22 were ground together with a solution of 15 g of calcium cyclamate, 3 g of polyvinyl pyrrolidone, 1 g of methyl parahydroxy benzoate and 1.9 g of a condensation product of octyl cresol with 8–10 moles of ethylene oxide in a ball mill for several hours to afford a suspension which was suitable for oral administration.

EXAMPLE 37

60 g of sodium glycerophosphate, 40 g of calcium glycerophosphate and 110 g of a compound as obtained according to Examples 1 to 22 were intimately blended, this mixture was gradually added to 850 g of soluble casein in a suitable mixer and mixed homogenously to afford a composition suitable for dietetic application.

EXAMPLE 38

A mixture of some grams of sodium dioctyl sulfosuccinate dissolved in an adequate amount of methanol, 520 g of a compound as obtained according to Examples 1 to 22, 70 g of corn starch and 10 g of alginic acid was granulated, while admixing an adequate amount of an aqueous 10% corn starch paste. The granules were screened while stirring through a 12 mesh U.S. standard sieve and dried at 50°–55° C. The dried granules were then screened through a 12 mesh U.S. standard sieve, 5 g of magnesium stearate were added and the mixture was compressed into tablets each containing 100 mg of active substance.

EXAMPLE 39

A mixture of 500 g of a compound as obtained according to Examples 1 to 22, 90 g of corn starch and 7 g of magnesium stearate was molded into shaped structures which were broken up into granules and screened through a sieve (8 mesh). The granules were then coated with an adequate amount of a mixture of 15 g of shellac, 3 g of olive oil and 800 g of ethyl alcohol. 3 g of magnesium stearate were added and the mixture was compressed into tablets each containing 250 mg of active substance.

We claim:

1. A dry pharmaceutical composition for lowering lipid and sugar levels in the blood of a human or animal suffering from hyperlipemia, said composition being in dosage unit form suitable for oral administration and comprising a physiologically acceptable excipient and 0.1 to 1 g of a metabolically active bis(4-hydroxyphenyl) alkanoic acid or ester thereof corresponding to the formula

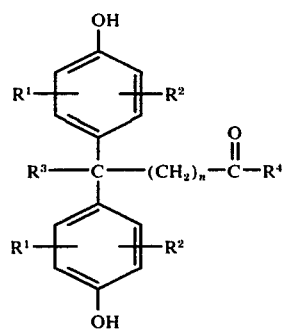

or

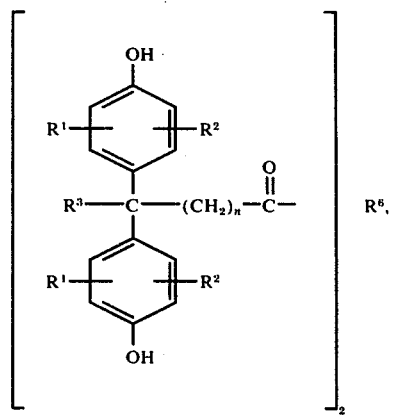

wherein
R$^1$ and R$^2$, which are the same or different, are each hydrogen, halogen, or alkyl having 1 to 4 carbon atoms;
R$^3$ is hydrogen or alkyl having 1 to 3 carbon atoms;
R$^4$ is hydroxy, alkoxy having 1 to 8 carbon atoms, phenyl-alkoxy having 1 to 4 alkyl carbon atoms, or cycloalkyl-oxy having 5 to 8 carbon atoms;

$R^6$ is alkylene having 2 to 12 carbon atoms; and
n is zero or an integer from 1 to 6.

2. The pharmaceutical composition as in claim 1 wherein said bis(4-hydroxy-phenyl) alkanoic acid is bis(4'-hydroxy-3',5'-di-tert.butyl-phenyl) ethanoic acid.

3. The pharmaceutical composition as in claim 1 wherein said bis(4-hydroxy-phenyl) alkanoic acid is 3,3-bis(4-hydroxy-3'-tert.butyl-phenyl) butanoic acid.

4. The pharmaceutical composition as in claim 1 wherein said bis(4-hydroxy-phenyl) alkanoic acid is bis(4'-hydroxy-3'-tert.butyl-phenyl) ethanoic acid.

5. The pharmaceutical composition as in claim 1 wherein said bis(4-hydroxy-phenyl) alkanoic acid ester is bis(4'-hydroxy-3'-tert.butyl-phenyl) ethanoic acid n-butyl ester.

6. The pharmaceutical composition as in claim 1 wherein said bis(4-hydroxy-phenyl) alkanoic acid ester is 3,3-bis(4'-hydroxy-3'-tert.butyl-phenyl) butanoic acid n-butyl ester.

7. The pharmaceutical composition as in claim 1 wherein said bis(4-hydroxy-phenyl) alkanoic acid is 4,4-bis(4'-hydroxy-3'-tert.butyl-phenyl) pentanoic acid.

8. The pharmaceutical composition as in claim 1 wherein said bis(4-hydroxy-phenyl) alkanoic acid ester is 4,4-bis(4'-hydroxy-3'-tert.butyl-phenyl) pentanoic acid n-butyl ester.

9. The pharmaceutical composition as in claim 1 wherein said bis(4-hydroxy-phenyl) alkanoic acid ester is bis[4,4-bis(4'-hydroxy-3'-tert.butyl-phenyl) pentanoic acid] glycol ester.

10. The pharmaceutical composition as in claim 1 wherein said bis(4-hydroxy-phenyl) alkanoic acid ester is bis[3,3-bis(4'-hydroxy-3'-tert.butyl-5'-bromophenyl)butanoic acid] glycol ester.

11. The pharmaceutical composition as in claim 1 which comprises 0.25 to 0.5 g of said active bis(4-hydroxyphenyl)alkanoic acid or ester.

12. The pharmaceutical composition as in claim 1 in the form of a capsule.

13. A method for lowering lipid and sugar levels in the blood of a human or animal suffering from hyperlipemia, which method comprises orally administering an effective amount of a bis(4-hydroxyphenyl) alkanoic acid or ester thereof corresponding to the formula

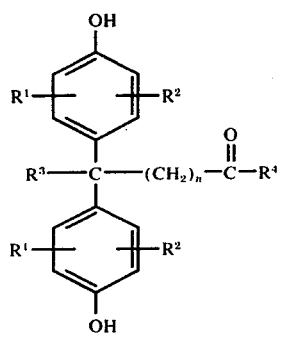

or

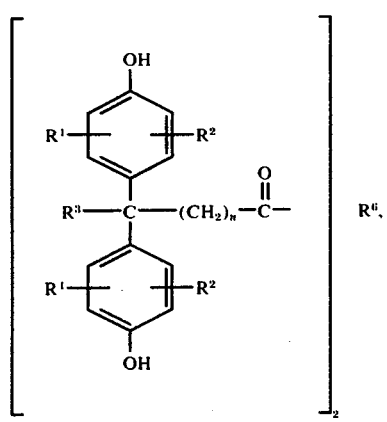

wherein
$R^1$ and $R^2$, which are the same or different, are each hydrogen, halogen, or alkyl having 1 to 4 carbon atoms;
$R^3$ is hydrogen or alkyl having 1 to 3 carbon atoms;
$R^4$ is hydroxy, alkoxy having 1 to 8 carbon atoms, phenyl-alkoxy having 1 to 4 alkyl carbon atoms, or cycloalkyl-oxy having 5 to 8 carbon atoms;
$R^6$ is alkylene having 2 to 12 carbon atoms; and
n is zero or an integer from 1 to 6.

* * * * *

Dedication

4,007,282.—*Otto Mauz*, Liederbach, Taunus, and *Ernold Granzer*, Kelkheim, Taunus, Germany. LOWERING LIPID AND SUGAR LEVELS IN THE BLOOD WITH A BIS(4-HYDROXYPHENYL) ALKANOIC ACID OR ESTER THEREOF. Patent dated Feb. 8, 1977. Dedication filed June 4, 1982, by the assignee, *Hoechst Aktiengesellschaft.*

Hereby dedicates said patent to the Public.

[*Official Gazette March 15, 1983.*]